(12) United States Patent
Choi et al.

(10) Patent No.: US 6,228,655 B1
(45) Date of Patent: May 8, 2001

(54) METHOD FOR DETECTION OF DNA ON POLYMER GELS USING A COUNTER-DYE COMPOSITION AND COUNTER-DYE COMPOSITION FOR THE SAME

(76) Inventors: Jung Kap Choi, Mirabo Apt. #305-807, Woonam-dong, Buk-ku, Kwangju 500-170; Da-Woon Jung, Woosanjukong Apt. #105-906, Moonheung-dong, Buk-ku, Kwangju 500-110; Gyurng Soo Yoo, Hyundai Apt. #203-1204, Yongbong-dong, Buk-ku, Kwangju 500-070, all of (KR)

( * ) Notice: Subject to any disclaimer, the term of this patent is extended or adjusted under 35 U.S.C. 154(b) by 0 days.

(21) Appl. No.: 09/351,116

(22) Filed: Jul. 10, 1999

Related U.S. Application Data (63) Continuation of application No. PCT/KR99/00104, filed on Mar. 4, 1999.

(30) Foreign Application Priority Data

Jul. 20, 1998 (KR) .................................................. 98-29105
Jan. 20, 1999 (KR) .................................................... 99-1674

(51) Int. Cl.[7] ................................................ G01N 33/483
(52) U.S. Cl. ........................ 436/94; 436/166; 536/25.32; 536/25.4
(58) Field of Search .............................. 436/94, 164, 166, 436/169, 174; 8/636, 657, 658; 536/25.32, 25.4; 435/40.5

(56) References Cited

U.S. PATENT DOCUMENTS 4,345,027   8/1982   Dolbeare .

FOREIGN PATENT DOCUMENTS

WO 97/13810   4/1997   (WO) .

OTHER PUBLICATIONS

Abstract: Na et al., Evans Bue Staining Method for Detection of Proteins on Polyacrylamide Gels with Rhodamine B, Anal. Lett. 27 (7) 1265–75 (abstract), 1994.*

Choi et al., A modified Coomassie Blue Staining of Proteins in Polyacrylamide Gels with Bismark Brown R, Anal. Biochem 236, 82–84, 1996.*

Chemical Abstracts, vol. 123, No. 17, Oct. 23, 1995, p. 250, col. 2, abstract No. 219500e.

Chemical Abstracts, vol. 92, No. 25, Jun. 23, 1980, p. 269, col. 1, abstract No. 211303p.

* cited by examiner

Primary Examiner—Jill Warden
(74) Attorney, Agent, or Firm—Peter F. Corless; Edwards & Angell, LLP (57) ABSTRACT

The present invention relates to a method for detection of DNA using a counter-dye composition containing two dyes of which electric charges are contrary to each other, on polymer gels, and the counter-dye composition for detection of DNA on polymer gels. More specifically, the present invention relates to a method for detection of DNA in a high sensitivity on polymer gels in a rapid, simple and safe manner, comprising the steps of staining the polymer gels with a counter-dye composition containing a cationic dye and an anionic dye and then macroscopically observing the gel without radiation of ultraviolet ray, and the counter-dye composition for detection of DNA on polymer gels.

5 Claims, 6 Drawing Sheets

METHOD FOR DETECTION OF DNA ON POLYMER GELS USING A COUNTER-DYE COMPOSITION AND COUNTER-DYE COMPOSITION FOR THE SAME

This application is a continuation of copending application International Application PCT/KR99/00104 filed on Mar. 4, 1999 and which designated the U.S.

TECHNICAL FIELD

The present invention relates to a method for detection of DNA using a counter-dye composition containing two dyes of which electric charges are contrary to each other, on polymer gels, and the counter-dye composition for detection of DNA on polymer gels. More specifically, the present invention relates to a method for detection of DNA in a high sensitivity on polymer gels in a rapid, simple and safe manner, comprising the steps of staining polymer gels with a counter-dye composition containing a cationic dye and an anionic dye and then macroscopically observing the gels without radiation of ultraviolet ray, and the counter-dye composition for detection of DNA on polymer gels.

BACKGROUND ART

In accordance with rapid development of techniques in the field of biotechnology including molecular biology, various analytical techniques which help the research activities in this technical field have also been developed from day to day. Particularly, the separation, purification and identification of DNA on polymer gels are the essential key techniques in the field of biotechnology and their use and importance have been increased. The separation and identification of DNA have generally been accomplished by electrophoresis on polymer gels such as agarose gels or polyacrylamide gels. Since polymer gels can be prepared in various types and sizes and their porosity can also be varied, polymer gels are of wide application. Although the polyacrylamide gel has an excellent separating ability sufficient to distinguish even the difference of 1 bp, it is suitable for the separation of small fragment DNAs having 5–500 bp because it can be applied only within the narrow range. Contrary to this, the agarose gel has been widely used due to its applicable range as broad as 200 bp–50 kb DNAs.

To detect DNA fragments separated on polymer gels, DNA staining method using Ethidium bromide (hereinafter, abbreviated to EB) has been the most generally used [see Sharp, P. A., Sugden, B. and Sambrook, J., Detection of two restriction endonuclease activities in *Haemophilus parainfluenzae* using analytical agarose-ethidium bromide electrophoresis, Biochemistry 12 (16), 3055–3063 (1973)]. EB has a planar aromatic ring-containing structure which can be intercalated into the helical structure of DNA, as represented by the following chemical formula (1) and is fixed between DNA bases to display an increased fluorescence upon radiation of ultraviolet ray:

(1)

The difference in fluorescences between EB combined to DNA and background EB allows to detect the DNA band and reaches about 40 times. The staining with EB is conducted by adding EB at a concentration of 0.5 μg/ml to electrophoresis buffer solution and an agarose gel and, after completion of electrophoresis, mounting the gel on a transilluminator and then applying the radiation of ultraviolet ray to the gel to detect the DNA band. Alternatively, the gel obtained after electrophoresis can be stained by immersing the gel into EB solution (0.5 μg/ml), washed with water and then mounted on a transilluminator to detect the DNA band [see Sambrook, J., Fritsch, E. F. and Maniatis, T.: Molecular Cloning: A Laboratory Manual, Cold Spring Harbor University Press (1989)].

Although the above-mentioned methods have been widely used because of their relatively simple procedure and high sensitivity (1–10 ng), they have serious problems as specifically described below. First, since EB is a potent mutagen, it must be substantially carefully handled and wasted. Second, since ultraviolet ray having short wavelength (254–310 nm) is radiated, the use of any shield for protection of experimenters from the radiation is required. Third, toxic substances such as ozone is produced by UV light; fourth, DNA damages such as DNA dimerization, nicking, bleaching, etc., may be caused upon UV radiation [see Brunk, C. F., Simson, L., Analytical Biochemistry 82, 455–462 (1977)]; and fifth, the photographing equipment is required to take photographs for obtaining the record of experimental result.

As the methods to improve the above-mentioned problems involved in EB staining method, silver staining method, method for detection of prestained DNA using confocal laser scanning fluorescence imaging system, staining method using imidazole and zinc, and staining method using a visible dye have been reported.

Although silver staining method has advantages that it has better sensitivity than EB and does not require UV radiation, its general use is limited due to very complicated procedure and high cost for purchasing reagents [see Datar, R. H. and Bhisey, A. N., A sensitive method for permanent silver staining of DNA in agarose gels, Indian Journal of Biochemistry & Biophysics 25, 373–375 (1988); Peats, S., Quantitation of protein and DNA in silver-stained agarose gels, Analytical Biochemistry 140, 178–182 (1984); Gottlieb, M. and Chavko, M., Silver staining of native and denatured eukaryotic DNA in agarose gels, Analytical Biochemistry 165, 33–37 (1987); and Beidler, J. L., Hilliard, P. R and Rill, R. L., Ultrasensitive staining of nucleic acids with silver, Analytical Biochemistry 126, 374–380 (1982)].

The method for detection of prestained DNA using confocal laser scanning fluorescence imaging system is conducted by subjecting DNA prestained with EB homodimer, oxazole yellow homodimer, thiazole orange homodimer, etc. to electrophoresis and then detecting the DNA by means of a confocal laser scanning fluorescence imaging system [see Ray, H. S., Quesada, M. A., Peck, K., Mathies, R. A. and Glazer, A. N., High-sensitivity two-color detection of double-stranded DNA with a confocal fluorescence gel scanner using ethidium homodimer and thiazole orange, Nucleic Acid Research 19 (2), 327–333 (1991)]. This method has the advantage of a very high sensitivity but has the disadvantage in that it requires the use of very expensive apparatus.

The staining method using imidazole and zinc ion is a method wherein DNA can be detected by combining $Zn^{2+}$ to DNA and then adding imidazole thereto to produce an insoluble white precipitate on DNA band [see Hardy, E., Sosa, A. E., Pupo, E., Casavilla, R. and Fernandez-Patron, C., Zinc-imidazole positive: A new method for DNA detection after electrophoresis on agarose gels not interfering with DNA biological integrity, Electrophoresis 17, 26–29 (1996)]. The other method using imidazole and zinc ion is a background staining method for DNA detection in which the precipitate of Zn2+-imidazole is produced on the gel surface except DNA band [see Hardy, E., Pupo, E., Casavilla, R., Sosa, A. E., Trujillo, L. E., Lopez, E. and Castellanos-Serra, L., Negative staining with zinc-imidazole of gel electrophoresis-separated nucleic acids, Electrophoresis 17, 1537–1541 (1996)]. The Zn2+-imidazole methods have some advantages that they use other reagents than toxic substances such as EB and their sensitivities are not lower than that of EB. Furthermore, since they do not require the use of UV radiation, the problems caused by UV radiation, including DNA damages, do not occur and they are suitable for preparative purpose. However, the methods have also disadvantages in that they are conducted through relatively complicated detection procedures, the permanent deposit of samples is impossible (the sample can be stored for only 2 months in distilled water), and the contrast between DNA band and background is visibly unclear.

The staining with a visible dye is a method in which a dye having the structure similar to that of EB, such as Brilliant cresyl blue, Nile blue, Methylene blue, etc., is used and DNA can be detected only through staining and destaining procedures without ultraviolet ray radiation. However, this has some disadvantages in that the staining and destaining procedures need a long time and the sensitivity is low (15–40 ng). For example, using Methylene blue, it takes from 2 hours to a few days for destaining procedure. The sensitivity is 25 ng using Brilliant cresyl blue, 40 ng using Nile blue and 15–20 ng using Methylene blue, respectively [see Santillan-Torres, J. L. and Ponce-Noyola, P., A novel stain for DNA in agarose gels, Trend genet 9 (2), 40 (1993); and Adkins, S. and Burmeister, M., Visualization of DNA in agarose gels as migrating colored bands: Applications for preparative gels and educational demonstrations, Analytical Biochemistry 240, 17–23 (1996)].

In addition to the above-mentioned methods, the method for detection of DNA combined to biotin on agarose gels without blotting procedure has also been reported [see Sun, Y., Detection of biotinylated nucleic acids directly on agarose gels, Biotechniques 16 (5), 782–784 (1994)]. However, this is also conducted through complicated procedures.

In another aspect, Janus blue is a cationic dye having the structure containing a quaternary amine and a planar aromatic ring which can be intercalated into DNA helix. Literature [Dutt M K, Microsc Acta, 1982, 85 (4), 361–368] describes a method for staining cell nuclei from tissue section in which RNA has been selectively extracted with cold phosphate buffer solution, using an aqueous solution containing Janus blue, Methylene blue and Janus red. However, this differs in a good deal from the method for detection of DNA on polymer gels according to the present invention. Literature [Steve Adkins et al., Analytical Biochemistry 240, 17–23, 1996] describes that by inclusion of various common commercially available visible dyes (such as Crystal violet, Methyl green, Pyronin Y, Thionin, Basic blue 66, Basic red 29, Safranin O, Janus green B, Nile blue, Pinacyanol, Stains-all, Basic yellow 11, Alcian blue 8GX, and Ruthenium red) in standard agarose gels, DNA bands are observable in visible light as they are separating. According to the above literature, such bands could be directly recovered from gels (approximately 50% yield) and used in standard enzymatic reactions without purification and of common commercially available dyes, Nile blue gave the sharpest and most persistent bands. Additionally, they reported that bands containing greater than 40 ng DNA could be detected by direct visual inspection of gels during electrophoresis and drying the gels increased sensitivity to 4 ng. However, it differs from the present invention in staining method and has drawbacks in that it has low detection sensitivity.

Thus, the present inventors have extensively and repeatedly studied for improvement of the prior staining method with visible dye in order to develop the method for detection of DNA in a sensitivity comparable to that of EB staining method and in a rapid, simple and safe manner, which can be used as a substitute for the prior EB staining method involving the problems which may be caused by toxicity and mutagenicity of EB itself and by the radiation of ultraviolet ray which is harmful to DNA sample and human body. As a result, we have found that the above-mentioned purpose can be attained by use of a counter-dye composition containing two kinds of dyes which have contrary electric charges to each other, i. e. a cationic dye and an anionic dye, and have completed the present invention.

DISCLOSURE OF THE INVENTION

Accordingly, the purpose of the present invention is to provide a method which can solve the problems involved in the above-mentioned prior methods. Thus, the present invention relates to a method for detecting DNA in a high sensitivity, which is comparable to that of the prior EB staining method, and in a rapid, simple and safe manner, by staining polymer gels with a counter-dye composition containing two dyes of which electric charges are contrary to each other, and then macroscopically observing the gels without radiation of ultraviolet ray.

One aspect of the present invention provides a method for detection of DNA on polymer gels comprising the step of staining the polymer gels with a counter-dye composition containing a cationic dye and an anionic dye. Preferably, the composition contains Janus blue and Methyl orange, Crystal violet and Methyl orange, Nile blue and Methyl orange, or Methylene blue and Zincon. More preferably, the composition contains Janus blue and Methyl orange, or Crystal violet and Methyl orange. In the present composition, each of the cationic and anionic dyes preferably has a concentration of 0.001–0.1% by weight of the volume of the composition. First, in case the polymer gels are agarose gels, it is preferable that the composition contains Janus blue and Methyl orange in the molar ratio of 1 to 0.4–0.8 and fixer contains 10 v/v % ethanol-0.2M sodium acetate buffer of pH 4.7. Second, in case the polymer gels are polyacrylamide gels, it is preferable that the composition contains Janus blue and Methyl orange in the molar ratio of 1 to 1–1.5 and further contains an 40 v/v % aqueous methanol solution.

Another aspect of the present invention provides a counter-dye composition for detection of DNA on polymer gels containing a cationic dye and an anionic dye. Preferably, the composition contains Janus blue and Methyl orange, Crystal violet and Methyl orange, Nile blue and Methyl orange, or Methylene blue and Zincon. More preferably, the composition contains Janus blue and Methyl orange, or Crystal violet and Methyl orange. In the present composition, each of the cationic and anionic dyes preferably has a concentration of 0.001–0.1% by weight of the volume of the composition. First, in case the polymer gels are agarose gels, it is preferable that the composition contains Janus blue and Methyl orange in the molar ratio of 1 to 0.4–0.8 and further contains 10 v/v % ethanol-0.2M sodium acetate buffer of pH 4.7. Second, in case the polymer gels are polyacrylamide gels, it is preferable that the composition contains Janus blue and Methyl orange in the molar ratio of 1 to 1–1.5 and further contains 40 v/v % aqueous methanol solution.

BEST MODE FOR CARRYING OUT THE INVENTION

Hereinafter, the present invention will be more specifically explained.

The cationic dye which can be used in the present invention includes Janus blue (formula 2), Crystal violet (formula 3), Nile blue (formula 4) and Methylene blue (formula 5). The anionic dye which can be used in the present invention includes Methyl orange (formula 6) and Zincon (formula 7).

(2)

(3)

(4)

(5)

(6)

(7)

In the present invention, it is very important to appropriately match the cationic dye and the anionic dye. In view of this, the counter-dye composition containing Janus blue and Methyl orange, the counter-dye composition containing Crystal violet and Methyl orange, the counter-dye composition containing Nile blue and Methyl orange, or the counter-dye composition containing Methylene blue and Zincon is preferable, and among the above compositions, the counter-dye composition containing Janus blue and Methyl orange, or the counter-dye composition containing Crystal violet and Methyl orange is more preferable, and the counter-dye composition containing Janus blue and Methyl orange is most preferable.

Since precipitate is likely to be formed due to the formation of ion-pair between a cationic dye and an anionic dye, the composition is preferably prepared by mixing the cationic dye and the anionic dye, immediately before its use. The counter-dye composition according to the present invention produces a fine precipitate with the lapse of time after preparation. In this case, excessive precipitate is not preferable because it interferes with the inflow of dye into gel background and also DNA band whereas the appropriate precipitate is preferable because it increases the intensity of DNA band in comparison to the gel background and improves the sensitivity of DNA detection.

Dyes which can replace the above-described dyes in the present invention are listed in the following Table 1. All of these dyes lie within the scope of the present invention.

TABLE 1

| Counter-dye composition | Dye | Replaceable dyes |
|---|---|---|
| Janus blue + Methyl orange | Janus blue | any salts thereof, Janus black, Janus green, Janus green B |
| | Methyl orange | any salts thereof, Sulfosalicylate, Xylenol orange |
| Crystal violet + Methyl orange | Crystal violet | any salts thereof including chloride salts, Basic violet 2, Methyl green, Brilliant green |
| | Methyl orange | any salts thereof including sodium, chloride, hydrazide salts, etc., Sulfosalicylate, Zincon, Methyl red |
| Nile blue + Methyl orange | Nile blue | any salts thereof including chloride, sulfate salts, Nile blue 2B, Nile blue A |
| | Methyl orange | any salts thereof including sodium, chloride, hydrazide salts, etc., Thymolphthalein, Bromothymol blue, Methyl red |

TABLE 1-continued

| Counter-dye composition | Dye | Replaceable dyes |
|---|---|---|
| Methylene blue + Zincon | Methylene blue | any salts thereof, New methylene blue NGG |
| | Zincon | any salts thereof, Bromothymol blue, Sulfosalicylate, Ferrozine, Chromotrope 2R |

In the present staining method using a counter-dye composition, a cationic dye is a main dye and an anionic dye is an assistant dye having counter-ion effects. That is, the anionic dye acts as counter-ion to form ion-pair with the cationic dye, thereby preventing the inflow of the cationic dye into polymer gels, so as to allow to shorten destaining time and to increase the relative intensity of DNA band. More specifically, according to the present method, for the staining, it takes 0.5–1 hour in the case of agarose gels and 15–30 minutes in the case of polyacrylamide gels. The destaining step is preformed by immersing the gel into an aqueous alcohol solution and water. The prior staining method with visible dye requires a long term destaining procedure for 2 hours to a few days whereas in the method of the present invention, only about 10–30 minutes is sufficient for the destaining. Accordingly, the present invention allows to shorten the destaining time. In addition, since the method of the present invention does not use EB having a high toxicity and mutagenicity and can omit the radiation of ultraviolet ray, it assures the safety of experimenters.

In particular, it is most preferable to use a counter-dye composition containing Janus blue and Methyl orange, because pre-treatment is not necessary and destaining step is rapid and simple. Therefore, the counter-dye composition containing Janus blue and Methyl orange will be described in more detail hereinafter.

Figure 1A:
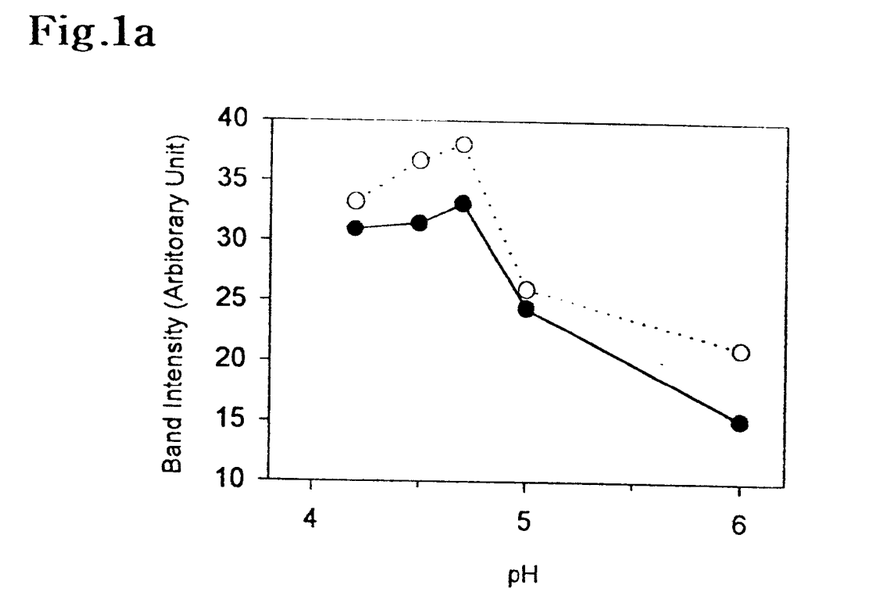
FIG. 1a is a graph which shows the intensity of DNA band on an agarose gel stained with a counter-dye composition containing Janus blue and Methyl orange according to pH.

Janus blue's DNA staining effects are changeable according to pH and the type of solvent in solution containing the dye. It was found that the intensity of DNA to background is highest in pH 4–5 of solution (see FIG. 1a; -○-; 9 kb DNA, -●-; 6 kb DNA). Particularly, since DNA may be damaged in low pH, agarose gels are preferably stained in about pH 4.7. In the case of staining with Janus blue alone, sensitivity may be decreased due to relatively high intensity of background. However, staining with Janus blue in combination with Methyl orange as a counter-ion, the intensity of DNA band increases whereas that of background is not changed much with the lapse of time, so as to increase the sensitivity of DNA detection.

Figure 1B:
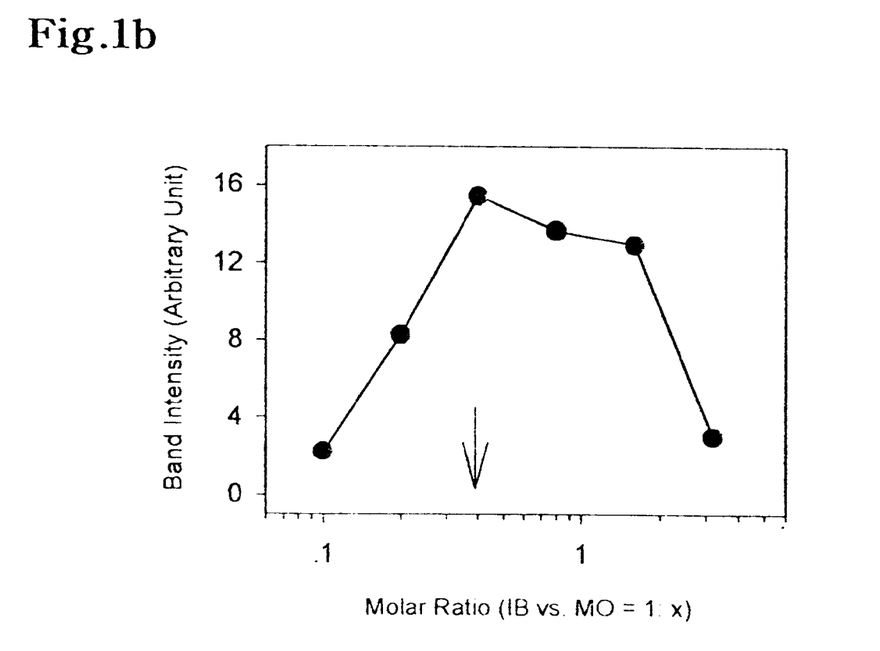
FIG. 1b is a graph which shows the intensity of DNA band on an agarose gel according to the molar ratio of Janus blue to Methyl orange.
Figure 2A:
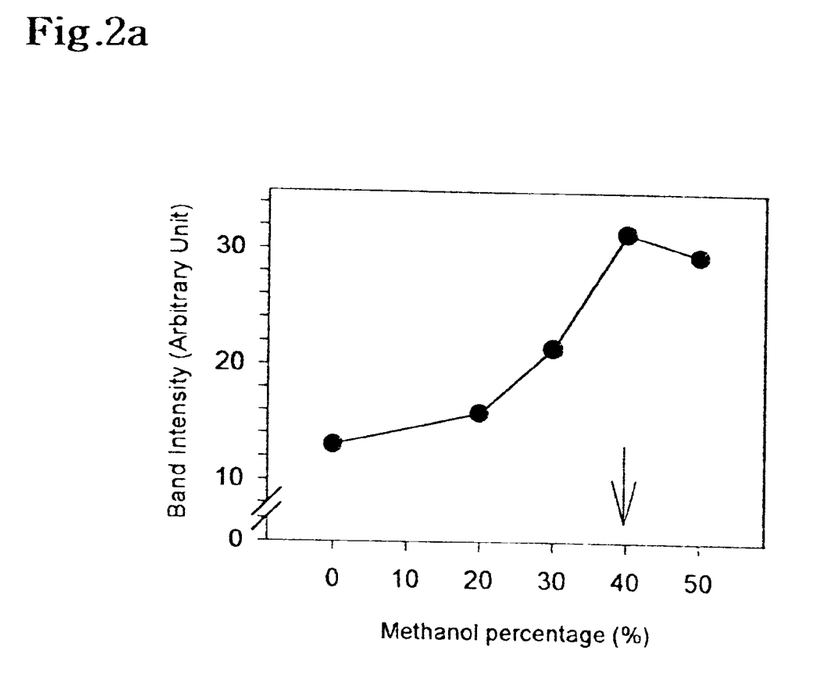
FIG. 2a is a graph which shows the intensity of DNA band stained with a counter-dye composition containing Janus blue and Methyl orange on a polyacrylamide gel according to the content ratio of methanol.
Figure 2B:
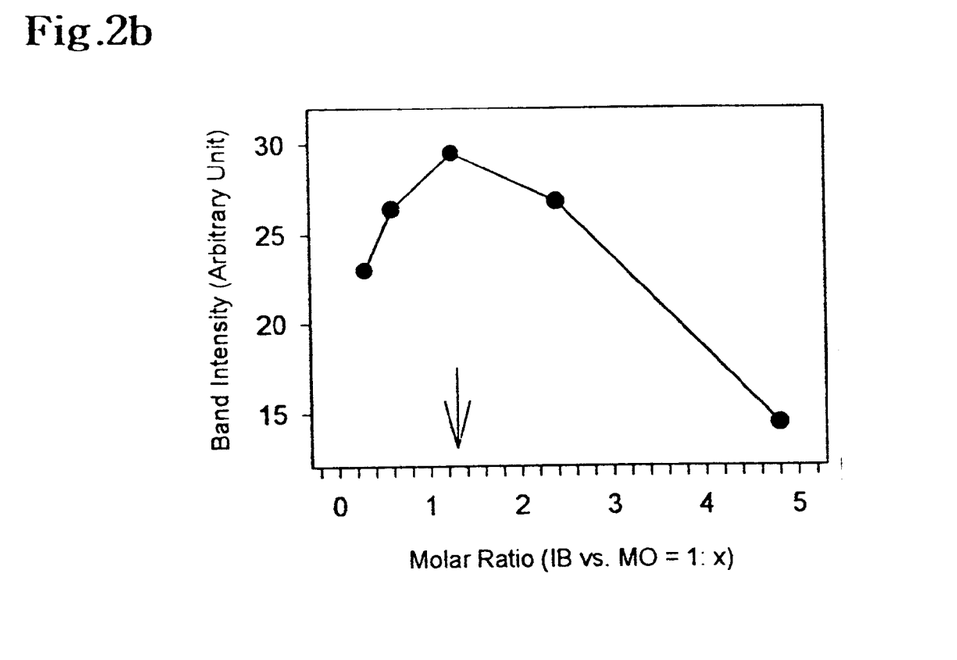
FIG. 2b is a graph which shows the intensity of DNA band on a polyacrylamide gel according to the molar ratio of Janus blue to Methyl orange.

The intensity of DNA band according to the ratio of Janus blue (abbreviated to IB) to Methyl orange (abbreviated to MO) is shown in FIGS. 1b (the intensity of DNA band on an agarose gel) and 2b (the intensity of DNA band on a polyacrylamide gel). FIGS. 1b and 2b show that the intensity of DNA band is high when the molar ratio of Janus blue to Methyl orange is 1 to 0.4–0.8, particularly 1 to 0.4, on the agarose gel, and 1 to 1–1.5, particularly 1 to 1.26, on the polyacrylamide gel, respectively.

Figure 1C:
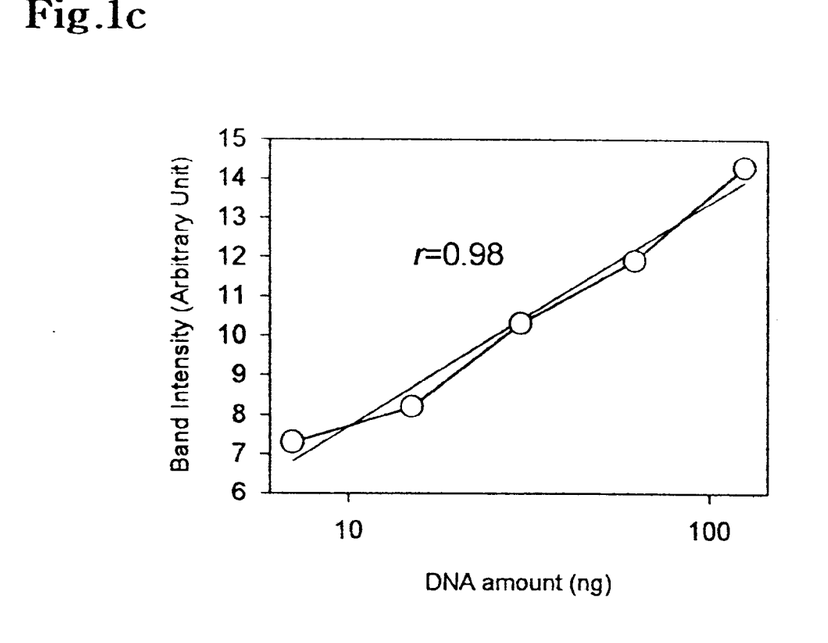
FIG. 1c is a graph which shows the intensity of DNA band stained with a counter-dye composition containing Janus blue and Methyl orange on an agarose gel according to a concentration of DNA.
Figure 2C:
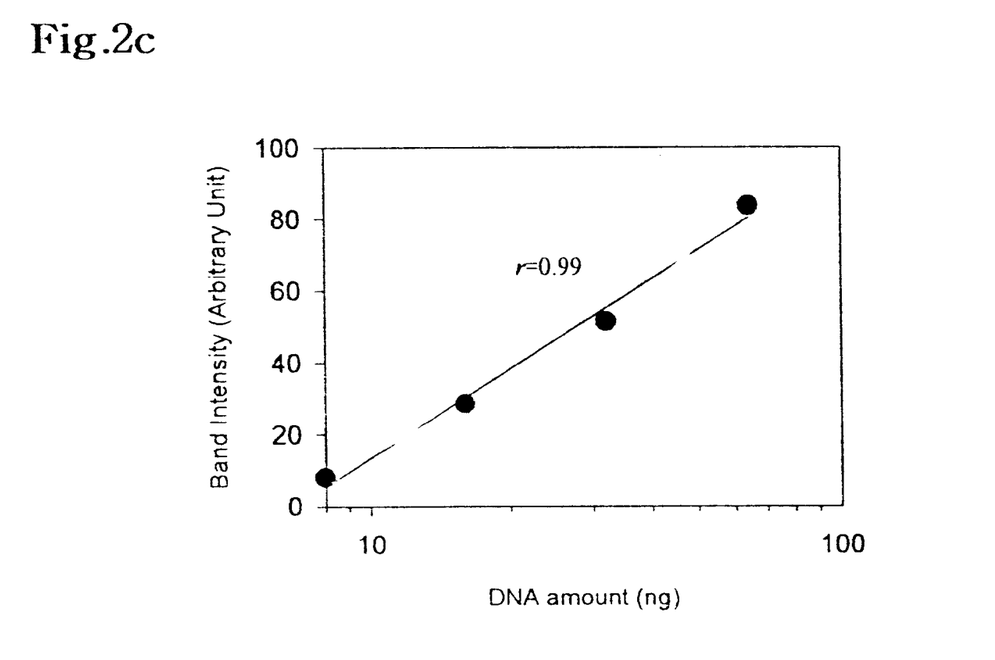
FIG. 2c is a graph which shows the intensity of DNA band stained with a counter-dye composition containing Janus blue and Methyl orange on a polyacrylamide gel according to a concentration of DNA.

In the present invention, particle size of dye is important and representative factors having effects thereon are i) a concentration and mixing molar ratio of dye, ii) a concentration and kind of solvent, and iii) a concentration of hydrogen ion. Mixing molar ratios of a cationic dye and an anionic dye are changed with characteristics of the dyes. It is desirable to mix the dyes in the optimal ratio in which excessive precipitates are not formed and the intensity of band to background is highest (see Table 2). Most preferably, agarose gels may be stained with agitation for 30–60 minutes using a counter-dye composition containing 10 v/v % ethanol-0.2M sodium acetate buffer (pH 4.7) as a solvent, and 0.007 w/v % of Janus blue and 0.00125 w/v % of Methyl orange (Janus blue:Methyl orange=1:0.4 by mole). Additionally, polyacrylamide gels may be stained with agitation for 15–20 minutes using a counter-dye composition containing 40 v/v % aqueous methanol solution as a solvent (see FIG. 2a which shows the intensity of DNA according to the content ratio of methanol), and 0.007 w/v % of Janus blue and 0.004 w/v % of Methyl orange (Janus blue:Methyl orange=1:1.26 by mole), after electrophoresis buffer solution is washed with distilled water for 5 minutes. Under the just above-described condition, since the inflow of dyes into background can be minimized and binding of dyes with DNA may not be interfered, it is possible to form particle size in which dyes can be efficiently adsorbed to DNA band. FIGS. 1c and 2c show the intensity of DNA band according to a concentration of DNA on an agarose gel and a polyacrylamide gel, respectively, which are stained with a counter-dye composition containing Janus blue and Methyl orange. They show that the intensity of DNA band increase quantitatively with the increase of DNA concentration.

The present invention is more specifically explained by the following examples. However, it should be understood that these examples are provided for more clear understanding of the constitution and effects of the present invention and are not intended to limit the scope of the present invention in any manners.

EXAMPLES 1 to 4

Detection of DNA on Agarose Gels Using a Counter-Dye Composition 1 g of agarose (Sigma, St. Louise, Mo., U.S.A.) was dissolved in 0.5×TBE buffer to prepare 100 ml of 1% agarose which was then molten in a microwave oven, poured into the mold and then solidified to obtain agarose gel having a thickness of 3 mm. 45 mM Tris-borate and 0.001M EDTA were contained in 0.5×TBE electrophoresis buffer solution which was introduced into the electrophoresis tank (MUPID 21, Cosmo Bio Co., Ltd., Japan). λ DNA/HindIII digest, which has been widely used as DNA marker, was diluted by two steps and then mixed with the loading buffer solution for DNA sample to prepare the DNA sample solution containing 10% glycerol and 0.05% Bromophenol blue. The sample solutions containing 167, 83, 42, 21, 10, 5, 2.5 ng of λ DNA/HindIII digest, respectively, were added to Nos. 1 to 7 of wells of agarose gel and the electrophoresis was conducted by developing the gel at 120V/30 cm for 1.5 hours.

Figure 3A:
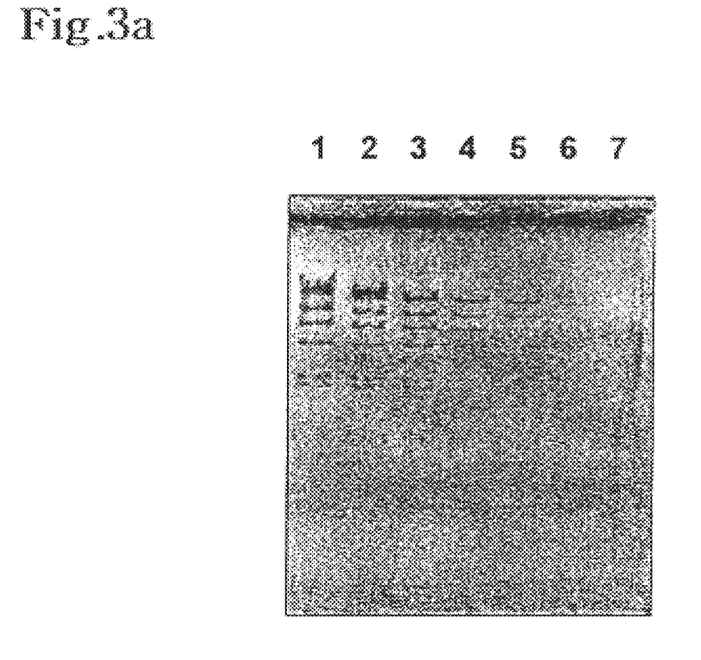
FIGS. 3a to 3c are photographs which show the detection sensitivities of DNA on agarose gels using Janus blue-Methyl orange staining method (a), Crystal violet-Methyl orange staining method (b), and EB staining method (c), respectively.
Figure 3B:
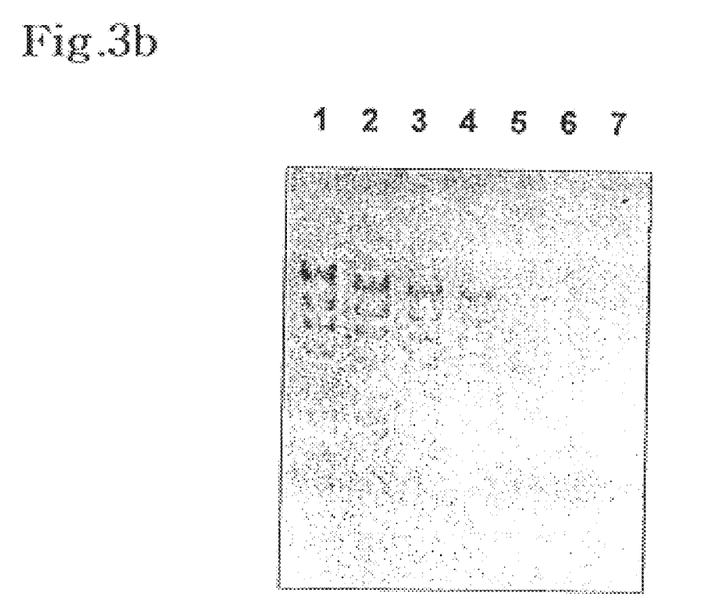

After completion of electrophoresis, staining was performed using a counter-dye composition under the condition as described in the following Table 2, respectively. Particularly, in the case of using Janus blue and Methyl orange (Example 1), the gel was stained for 1 hour with agitation after immersing the gel into 10 v/v % ethanol-0.2M sodium acetate buffer (pH 4.7) containing 0.007 w/v % of Janus blue (Aldrich Chem., Co., ; content; 70%, MW 506.01) and 0.00125 w/v % of Methyl orange (Junsei Chem. Co., Ltd.; MW 327.34). After completion of staining, the gel was dried. If necessary, it was washed for 30 minutes with an alcohol-containing buffer to remove excessive dyes and dried. The results of Examples 1 and 2 (using Janus blue-Methyl orange and Crystal violet-Methyl orange, respectively) are shown in FIGS. 3a and 3b, respectively.

TABLE 2

| Example | dyes | final conc. (optimal conc.) (w/v %) | pre-treatment (time) | solvent | staining time (min) | destaining |
|---|---|---|---|---|---|---|
| 1 | Janus blue | 0.001–0.01 (0.007) | — | 10 v/v % ethanol- 0.2 M sodium acetate buffer (pH 4.7) | 60 | if necessary, in 60 v/v % methanol –0.2 M sodium acetate buffer (pH 4.7) for 30 min, then immersed in D.W. or dried |
| | Methyl orange | 0.001–0.01 (0.00125) | | | | |
| 2 | Crystal violet | 0.001–0.01 (0.005) | 40 v/v % aqueous methanol soln. | 20 v/v % aqueous methanol soln. | 60 | in 50 v/v % aqueous methanol solution for 20–30 sec, then immersed in 0.001% aqueous methyl orange soln. |
| | Methyl orange | 0.001–0.01 (0.006) | | | | |
| 3 | Nile blue | 0.001–0.1 (0.08) | — | 10 v/v % ethanol- 0.2 M sodium acetate buffer (pH 4.7) | 30 | If necessary, in 60 v/v % methanol –0.2 M sodium acetate buffer (pH 4.7) for 30 min, then immersed in D.W. or dried |
| | Methyl orange | 0.001–0.1 (0.03) | | | | |
| 4 | Methylene blue | 0.001–0.1 (0.03) | — | water | 20 | If necessary, in 60 v/v % aqueous |

TABLE 2-continued

| Example | dyes | final conc. (optimal conc.) (w/v %) | pre-treatment (time) | solvent | staining time (min) | destaining |
|---|---|---|---|---|---|---|
| | Zincon | 0.001–0.1 (0.03) | | | | ethanol soln. for 10 min, then immersed in D.W. or dried |

EXAMPLES 5 to 8

Detection of DNA on Polyacrylamide Gels Using a Counter-Dye Composition

30% acrylamide, distilled water, 5×TBE, 10% ammonium sulfate and TEMED were mixed and the resulting mixture was poured into the mold and solidified to prepare the polyacrylamide gel. 1×TBE buffer solution (98 mM Tris-borate, 2 mM EDTA, pH 8.0) was prepared and then introduced into the reservoir of electrophoresis apparatus. 800, 400, 200, 100, 50, 25, 12.5 ng of phage X174 DNA/HaeIII digest samples (containing sample loading buffer solution) were loaded respectively onto the wells of polyacrylamide gel from No. 1 of well and then electrophoresis was conducted at 100V for 1 hour.

Figure 4A:
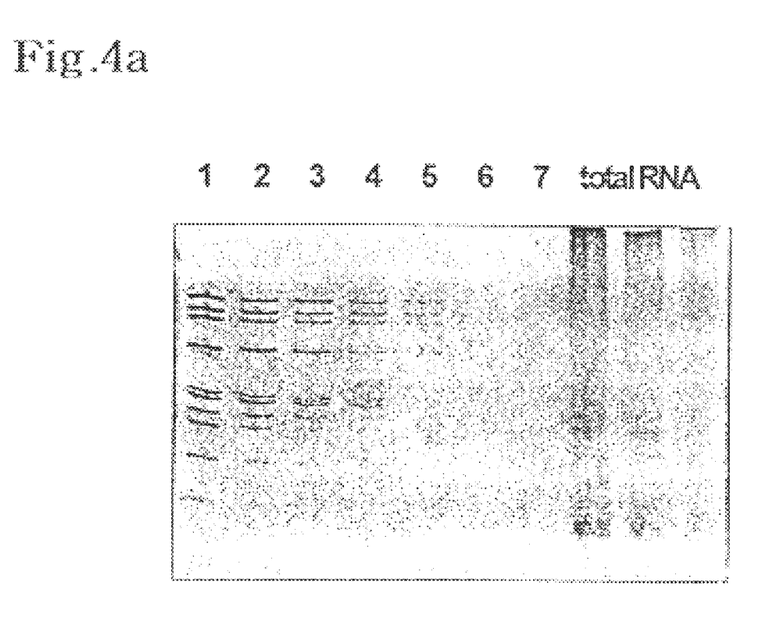
FIGS. 4a to 4c are photographs which show the detection sensitivities of DNA on polyacrylamide gels using Janus blue-Methyl orange staining method (a), Crystal violet-Methyl orange staining method (b), and EB staining method (c), respectively.
Figure 4B:
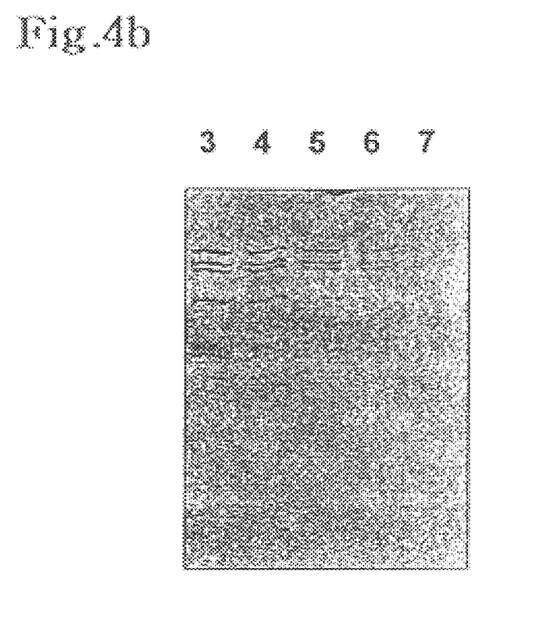

After completion of electrophoresis, the polyacrylamide gel was stained with a counter-dye composition under the condition as described in the following Table 3. Particularly, in the case of using Janus blue and Methyl orange, the gel was stained for 20 minutes with mild agitation after immersing the gel into 40 v/v % aqueous methanol solution containing 0.007 w/v % of Janus blue and 0.004 w/v % of Methyl orange. After completion of staining, the gel was dried. If necessary, it was washed for 10 minutes with 40 v/v % methanol and distilled water, respectively. The results of Examples 5 and 6 (using Janus blue-Methyl orange and Crystal violet-Methyl orange, respectively) are shown in FIGS. 4a and 4b, respectively.

TABLE 3

| Example | dyes | final conc. (optimal conc.) (w/v %) | pre-treatment (time) | solvent | staining time (min) | destaining |
|---|---|---|---|---|---|---|
| 1 | Janus blue Methyl orange | 0.001–0.01 (0.007) 0.001–0.01 (0.004) | D.W. (5 min) | 40 v/v % aqueous methanol soln. | 20 | if necessary, in 40 v/v % aqueous methanol solution for 10 min and in D.W. for 10 min, then dried |
| 2 | Crystal violet Methyl orange | 0.001–0.01 (0.005) 0.001–0.01 (0.004) | D.W. (5 min) | D.W. | 20 | in 50 v/v % aqueous methanol solution for 5-10 sec, then immersed in D.W. |
| 3 | Nile blue Methyl orange | 0.001–0.1 (0.008) 0.001–0.1 (0.005) | 40 v/v % aqueous methanol soln. (15 min) | 40 v/v % aqueous methanol soln. | 20 | if necessary, in 40 v/v % aqueous methanol soln. for 10 min and in D.W. for 10 min, then dried |
| 4 | Methylene blue Zincon | 0.001–0.1 (0.006) 0.001–0.1 (0.0035) | D.W. (5 min) | D.W. | 15 | if necessary, in 40 v/v % aqueous methanol soln. for 10 min and in D.W. for 10 min, then dried |

The detection sensitivities of Examples 1 to 8 are shown in the following Table 4.

TABLE 4

| Example | 1 | 2 | 3 | 4 | 5 | 6 | 7 | 8 |
|---|---|---|---|---|---|---|---|---|
| detection sensitivity (ng) | 2–20 | 2–20 | 4–40 | 2–20 | 1–10 | 1–10 | 1–10 | 1–10 |

COMPARATIVE EXAMPLE 1

Figure 3C:
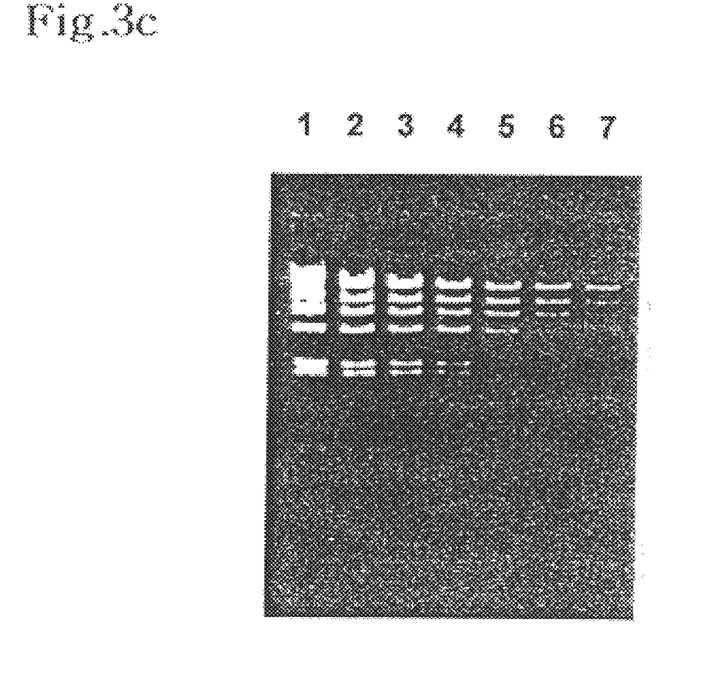

The electrophoresis was conducted in the substantially same manner as in Examples 1 to 4. Then, the agarose gel was immersed into 0.5 μg/ml of aqueous EB solution (Sigma) for 40 minutes to one hour, washed with distilled waster for 5 minutes and then observed on ultraviolet ray (302 nm) transilluminator. A photograph of the gel was taken with a polaroid camera. The result is shown in FIG. 3c. The detection sensitivity was determined as 1–10 ng.

COMPARATIVE EXAMPLE 2

Figure 4C:
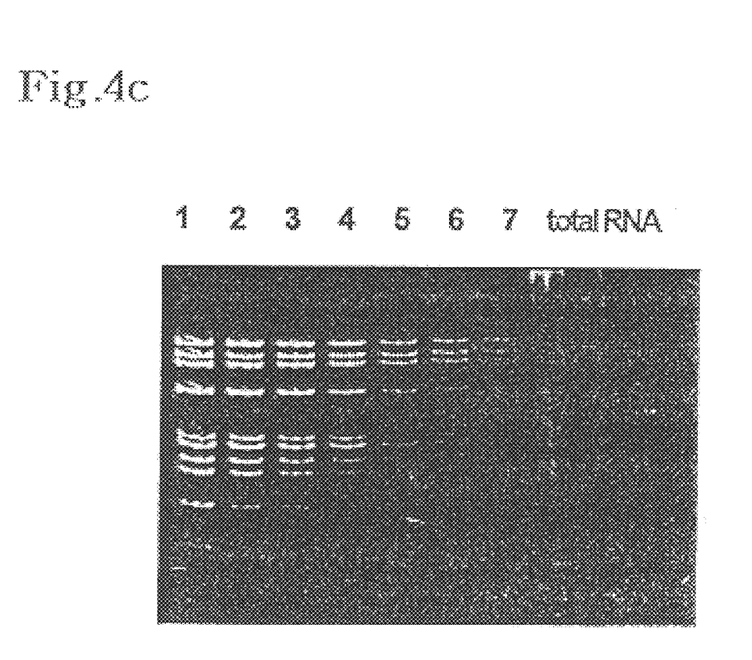

The electrophoresis was conducted in the substantially same manner as in Examples 5 to 8. Then, the polyacrylamide gel was immersed into 0.5 μg/ml of aqueous EB solution (Sigma) for 30–40 minutes, washed with distilled waster for 5 minutes and then observed on ultraviolet ray (302 nm) transilluminator. A photograph of the gel was taken with a polaroid camera. The result is shown in FIG. 4c.

From the above Examples and Comparative Examples, it can be seen that by using the counter-dye staining method according to the present invention, EB having a high toxicity and mutagenicity is replaced by a unique safe counter-dye composition, the radiation of ultraviolet ray can be omitted, the time for staining and destaining is shortened, and the DNA on polymer gels can be detected in a high sensitivity comparable to that of the prior EB staining method.

Since the method of the present invention can replace EB, which is difficult to handle and waste due to its high toxicity and mutagenicity, by a unique safe counter-dye composition and does not use the radiation of ultraviolet ray, the method for detection of DNA on polymer gel according to the present invention can safely, rapidly and simply detect DNA in a high sensitivity comparable to that of the prior EB staining method. Accordingly, the present invention apparently provides the improvement in the relevant technical field.

What is claimed is:

1. A method for detection of DNA on polymer gels comprising the step of staining the polymer gels with a counter-dye composition containing a cationic dye and an anionic dye selected from the group consisting of Janus blue and Methyl orange, Crystal violet and Methyl orange, Nile blue and Methyl orange, and Methylene blue and Zincon, wherein DNA complexes with the counter-dye composition, and observing DNA-counter-dye composition complexes.

2. The method according to claim 1, wherein the counter-dye composition contains Janus blue and Methyl orange, or Crystal violet and Methyl orange.

3. The method according to claim 1, wherein each of the cationic dye and the anionic dye has a concentration of 0.001–0.1% by weight of the volume of the composition.

4. The method according to claim 2, wherein the polymer gels are agarose gels, and the counter-dye composition contains Janus blue and Methyl orange in the molar ratio of 1 to 0.4–0.8 and further contains 10 v/v % ethanol-0.2M sodium acetate buffer of pH 4.7.

5. The method according to claim 2, wherein the polymer gels are polyacrylamide gels, and the counter-dye composition contains Janus blue and Methyl orange in the molar ratio of 1 to 1–1.5, and further contains 40 v/v % aqueous methanol solution.

* * * * *